United States Patent [19]

Shiozawa et al.

[11] Patent Number: 4,820,674

[45] Date of Patent: Apr. 11, 1989

[54] PROCESS FOR PREPARING A HYDROSILYLATION CATALYST

[75] Inventors: Kouji Shiozawa, Saitama; Yoshiharu Okumura, Tokyo; Chihiro Imai, Kanagawa; Nobukazu Okamoto, Saitama, all of Japan

[73] Assignee: Toa Nenryo Kogyo Kabushiki Kaisha, Tokyo, Japan

[21] Appl. No.: 149,092

[22] Filed: Jan. 27, 1988

[30] Foreign Application Priority Data

Jan. 29, 1987 [JP] Japan .................................. 62-18916

[51] Int. Cl.⁴ ............................................. B01J 31/00
[52] U.S. Cl. ................................... 502/169; 502/172; 502/230
[58] Field of Search ....................... 502/169, 172, 230; 556/479, 136; 549/206, 211

[56] References Cited

U.S. PATENT DOCUMENTS

| | | | |
|---|---|---|---|
| 3,220,972 | 11/1965 | Lamoreaux | 502/169 |
| 3,624,119 | 11/1971 | Rothe | 502/169 |
| 3,814,731 | 6/1974 | Nitzsche | 502/169 |

Primary Examiner—Patrick P. Garvin
Assistant Examiner—Elizabeth Irzinski
Attorney, Agent, or Firm—Wenderoth, Lind and Ponack

[57] ABSTRACT

A process for preparing a hydrosilylation catalyst by dissolving chloroplatinic acid $H_2PtCl_6$ in a cyclic ether or cyclic ester containing at least 3 carbon atoms, and maintaining the resulting solution at a temperature of at least 30° C.

4 Claims, No Drawings

PROCESS FOR PREPARING A HYDROSILYLATION CATALYST

BACKGROUND OF THE INVENTION

This invention relates to a process for preparing a hydrosilylation catalyst which is preferably used in synthesizing a silane coupling agent and, more particularly, to a process for preparing a hydrosilylation catalyst which is preferably used in synthesizing, by hydrosilylation reaction, a silane coupling agent of which demand is enlarged as an indispensable material in the development of ultrafasionable composite materials.

Heretofore, the following catalysts or processes (1) to (4) have been known as catalysts or processes which are used in synthesizing silane coupling agents by a hydrosilylation reaction. However, any of these catalysts or processes present problems as described hereinafter:

(1) as solution of chloroplatinic acid $H_2PtCl_6 \cdot 6H_2O$ in isopropanol (see J.Amer.Chem.Soc., VOL.82, 3602(1960)).

This catalyst requires a considerably long period (generally called induction period) until it exhibits a steady catalytic activity. Further, it must be pretreated with a portion of a reaction reagent prior to the reaction.

(2) A platinum-beta-diketone complex (see Japanese Patent Publn. No.24947/1975).

When this catalyst is used, hydrosilylated products can be obtained in a relatively high yield by a reaction of allyl chloride and trichlorosilane as described in the Japanese Patent Publn. However, the reaction temperature is high, the reaction time is long, and the preparation of the catalyst takes a long time.

(3) A process wherein a choloroplatinic acid catalyst is used in the presence of phenothiazine, diphenylamine or the like (Japanese Patent Publn, No.29873/1981)

When this process is utilized, the induction period of the catalyst is reduced and it is possible to lower the reaction temperature. However, the yield of hydrosilylated objective products is low.

(4) A Reaction product of chloroplatinic acid and cyclohexanone (Japanese Patent publn. No.41132/1978)

When this catalyst is used, hydrosilylated products which are objective products are obtained in a relatively high yield. However, cyclohexanone reacts with silane compounds such as trichlorosilane.

It is therefore an object of the present invention to provide a process for preparing a hydrosilylation catalyst which meets the following requirements: (1) the preparation of the catalyst is simple; (2) the induction period can be shortened; (3) the catalyst or the auxiliary catalyst is not consumed, and (4) the reaction proceeds under mild conditions and the silane coupling agent can be obtained in a high yield.

SUMMARY OF THE INVENTION

The present invention relates to a process for preparing a hydrosilylation catalyst wherein the long induction period which was the drawback of the prior catalyst can be eliminated or shortened by subjecting chloroplatinic acid $H_2PtCl_6$ heretofore used in this reaction as the catalyst to predetermined treatment.

A process for preparing a hydrosilylation catalyst according to the present invention comprises the steps of dissolving chloroplatinic acid $H_2PtCl_6$ in an ether or ester containing at least 3 carbon atoms, and retaining the resulting solution at a temperature of at least 30° C., preferably from 50° to 120° C.

DETAILED DESCRIPTION OF THE INVENTION

A process for preparing a hydrosilylation catalyst according to the present invention will be fully described hereinafter.

First, starting materials, reaction conditions and the like used in preparing a hydrosilylation catalyst according to the present invention are described in detail.

(1) ETHERS

Linear or cyclic ethers containing at least 3 carbon atoms such as ethyl ether, butyl ether, phenyl ether, anisole, tetrahydrofuran, furan, tetrahydropyran, and dioxane can be used herein. The preferred ethers are those containing no aliphatic multiple bonds.

Of these, tetrahydrofuran is particularly preferred.

The amount of these ethers used is usually at least 1 mole per 1 mole of chloroplatinic acid, particularly preferably from 100 to 2,000 moles. There is no upper limit thereof. It is possible to use the ethers as solvents for the hydrosilylation reaction in producing the silane coupling agent.

(2) ESTERS

Linear or cyclic esters containing at least 3 carbon atoms such as methyl acetate, amyl acetate, methyl propionate, ethyl benzoate, dimethyl phthalate, gamma-butyrolactone, delta-valerolactone, and epsilon-caprolactone can be used herein. The preferred esters are those containing no aliphatic multiple bonds.

Of these, gamma-butyrolactone is particularly preferred.

The amount of the esters used is the same as that of the ethers described above.

(3) PREPARATION OF HYDROSILYLATION CATALYST

In order to prepare a hydrosilylation catalyst (the reaction product of chloroplatinic acid and ether or ester) according to the present invention, chloroplatinic acid is dissolved in the ether or ester described above, and preferably, the mixture is heated under a nitrogen atmosphere usually for at least 5 minutes, preferably for 30 minutes to 2 hours. The heating temperature is at least 30° C., preferably from 50° C. to 120° C. When the boiling point of the ethers or esters used is lower than this temperature range, the mixture is heated to a temperature below the boiling point of the ethers or esters. While thus obtained reaction product of chloroplatinic acid and ethers or esters can be used as catalyst as it is, it is preferred that a desiccating agent such as anhydrous sodium sulfate, anhydrous sodium carbonate or sodium carbonate is usually added to the reaction product, and thereafter used as a hydrosilylation catalyst.

Among these desiccating agents, sodium carbonate and anhydrous sodium carbonate are particularly preferred because they can remove hydrogen chloride formed in the preparation step of the catalyst.

When chloroplatinic acid is dissolved in the ethers or esters and the solution is heated at a temperature at least 30° C., preferably from 50° C. to 120° C., it is believed that platinum is chloroplatinic acid is converted into a divalent state and platinum which is in a divalent state exhibits high catalytic activity towards the hydrosiiylation reaction. That is, according to the process for preparing the hydrosilylation catalyst based on the present invention, divalent platinum having high catalytic activity can be efficiently and readily formed.

When a small amount of the hydrosilylation catalyst formed by the present invention is added to, for example, an equimolar mixture of trichlorosilane and allyl chloride, a remarkable exothermic reaction rapidly occurs. When only chloroplatinic acid is added, such an exothermic reaction does not occur. Thus, when the hydrosilylation catalyst prepared by the present invention is used to carry out the hydrosilylation reaction, the hydrosilylation catalyst according to the present invention remarkably shortens the induction period also accompanying the exothermic reaction. (4) In order to use the hydrosilylation catalyst according to the present invention to synthesize a silane coupling agent by hydrosilylation reation, the hydrosilylation catalyst may be added to unsaturated compounds such as allyl chloride and allyl methacrylate (olefins) and silane compounds such as trichlorosilane and trimethoxy silane may be dropwise added, while maintaining the solution at a predetermined temperature. The amount of the hydrosilylation catalyst added is generally from $10^{-8}$ to $10^{-3}$ mole per mole of olefinic compounds on a platinum basis.

While the reaction temperature of hydrosilylation reaction is not particularly restricted, the proper reaction temperatures are usually in the range of from room temperature to 100° C. The particularly preferred reaction temperatures are from 30° C. to 80° C.

In carrying out the reaction as described above, solvents may or may not be used. When the solvents are used, generally, aromatic compounds are preferred.

The hydrosilylation catalyst according to the present invention can be applied to all of the hydrosilylation reactions.

Examples of olefinic compounds for use herein include monomers having aliphatic multiple bonds, allyl chloride, allyl methacrylate ester, allyl glycidyl ether, allyl amine and acrylonitrile. Silane compounds which react with these olefinic compounds are represented by the general formula:

$$HSiR_nX_{3-n}$$

wherein n is 0 or 1, R is an organic group such as a methyl, ethyl, or phenyl group, and X is so-called hydrolyzable group, for example, halogen, or alkoxy, acetoxy, isocyanate or azidoe group, particularly halogen or alkoxy group.

As stated hereinabove, if the hydrosilylation catalyst obtained by the process for preparing the hydrosilylation catalyst according to the present invention is used, the induction period for activating the catalyst can be remarkably shortened in carrying out the hydrosilylation reaction, and the reaction proceeds under mild conditions. Further, the side reaction can be inhibited and the silane coupling agent is obtained in a high yield. Furthermore, according to the present invention, the preparation of the hydrosilylation catalyst is easy.

While the present invention is illustrated by the following examples, the present invention is not limited thereto.

EXAMPLE 1

Preparation of Catalyst (A)

A three-neck flask equipped with a reflux condenser, stirring rod and thermometer was charged with one gram of chloroplatinic acid (IV) $H_2PtCl_6 \cdot 6H_2O$, and 200ml of tetrahydrofuran. The mixture was heated for one hour at the reflux temperature of tetrahydrofuran (about 65° C.) under a nitrogen atmosphere. The resulting solution was dried with anhydrous sodium sulfate to prepare a hydrosilylation catalyst. (Catalyst A)

EXAMPLE 2

Preparation of Catalyst (B)

A three-neck flask equipped with a reflux condenser, stirring rod and thermometer was charged with one gram of chloroplatinic aid (IV), and 200ml of gramma-butyrolactone. The mixture was heated for one hour at a temperature of 100° C. under a nitrogen atmosphere. The resulting solution was dried with anhydrous sodium sulfate to prepare a hydrosilylation catalyst (Catalyst B)

EXAMPLE 3

Preparation of Catalyst (C)

A three-neck flask equipped with a reflux condenser, stirring rod and thermometer was charged with one gram of chloroplatinic acid (IV) and 200ml of n-butyl ether. The mixture was heated for one hour at a temperature of 100° C. under a nitrogen atmosphere. The resulting solution was dried with anhydrous sodium sulfate to prepare a hydrosilylation catalyst. (Catalyst C)

EXAMPLE 4

A three-neck flask equipped with a reflux condenser, stirring rod and thermometer was charged with 7.6 grams of allyl chloride (0.1 mole) and one cubic centimeter of Catalyst A of Example 1 as a catalyst ($10^{-5}$ mole on a platinum basis). 13.5 grams of trichlorosilane (0.1mole) were dropwise added in one hour from a dropping funnel. The reaction temperature was maintained at about 40° C. The gas chromatography analysis demonstrated that gamma-chloropropyl trichlorosilane was obtained in a yield of 68% on an allyl chloride basis.

EXAMPLE 5

Example 4 was repeated except that catalyst B prepared by Example 2 was used as a catalyst. The gas chromatography analysis demonstrated that gamma-chloropropyl trichlorosilane was obtained in a yield of 66% on an allyl chloride basis.

EXAMPLE 6

Example 4 was repeated except that Catalyst C prepared by Example 3 was used as a catalyst. The gas chromatography analysis demonstrated that gamma-chloropropyl trichlorosilane was obtained in a yield of 55% on an allyl chloride basis.

COMPARATIVE EXAMPLE 1

A three-neck flack equipped with a reflux condenser, stirring rod and thermometer was charged with 7.6 grams of allyl chloride (0.1 mole) and a solution of chloroplatinic acid (IV) in isopropyl alcohol as a catalyst ($10^{-5}$ mole on a platinum basis). 13.5 grams of trichlorosilane (0.1 mole) were dropwise added in one hour from a dropping funnel. The reaction temperature was maintained at about 40° C. The gas chromatography analysis demonstrated that gamma-chloropropyl trichlorosilane was obtained in a yield of 23% on an allyl chloride basis.

EXAMPLE 7

A three-neck flask equipped with a reflux condenser, stirring rod and thermometer was charged with 50ml of toluene as a solvent, a small amount of polymerization inhibitor, 12.6 grams of allyl methacrylate ester (0.1 mole) and one cubic centimeter of Catalyst A of Example 1 as a catalyst ($10^{-5}$ mole on a platinum basis). 13.4 grams of trimethoxy silane (0.11 mole) were dropwise added in one hour from a dropping funnel. The reaction temperature was maintained at about 50° C. The reaction was further carried out for 30 minutes. The gas chromatography analysis demonstrated that gamma-methacryloxypropyl trimethoxy silane was obtained in a yield of 86% on an allyl methacrylate basis.

EXAMPLE 8

A three-neck flack equipped with a reflux condenser, stirring rod and thermometer was charged with 11.4 grams of allyl glycidyl ether (0.1 mole) and one cubic centimeter of Catalyst A of Example 1 as a catalyst ($10^{-5}$ mole on a platinum basis). 13.4 grams of trimethoxy silane (0.11 mole) were dropwise added in one hour from a dropping funnel. The reaction temperature was maintained at 50° C. The reaction was further carried out for 30 minutes. The gas chromatography analysis demonstrated that gamma-glycidyloxypropyl trimethoxy silane was obtained in a yield of 80%. on an allyl glycidylether basis.

What is claimed is:

1. A process for preparing a hydrosilylation catalyst which comprises the steps of dissolving chloroplatinic acid $H_2PtCl_6$ in a cyclic ether or cyclic ester containing at least 3 carbon atoms, and maintaining the resulting solution at a temperature of at least 30° C.

2. The process according to claim 1 wherein the ether is tetrahydrofuran.

3. The process according to claim 1 wherein the ester is gamma-butyrolactone.

4. The process according to claim 1 wherein the solution of chloroplatinic acid in the cyclic ether or cyclic ester is maintained at a temperature of from 50° to 120° C.

* * * * *